United States Patent
Pinchuk et al.

(10) Patent No.: US 9,044,301 B1
(45) Date of Patent: Jun. 2, 2015

(54) METHODS, SYSTEMS AND DEVICES FOR TREATING GLAUCOMA

(71) Applicant: InnFocus, Inc., Miami, FL (US)

(72) Inventors: Leonard Pinchuk, Miami, FL (US); John Martin, Miami, FL (US)

(73) Assignee: INNFOCUS, INC., Miami, FL (US)

( * ) Notice: Subject to any disclaimer, the term of this patent is extended or adjusted under 35 U.S.C. 154(b) by 0 days.

(21) Appl. No.: 14/511,802

(22) Filed: Oct. 10, 2014

Related U.S. Application Data (60) Provisional application No. 61/908,657, filed on Nov. 25, 2013.

(51) Int. Cl.
| | | |
|---|---|---|
| *A61M 27/00* | (2006.01) | |
| *A61F 9/007* | (2006.01) | |
| *A61F 9/008* | (2006.01) | |

(52) U.S. Cl.
CPC ..... *A61F 9/00781* (2013.01); *A61F 2220/0008* (2013.01); *A61M 27/002* (2013.01); *A61M 2210/0612* (2013.01); *A61F 9/007* (2013.01); *A61F 9/00736* (2013.01); *A61F 2009/00891* (2013.01)

(58) Field of Classification Search
CPC ............ A61M 27/002; A61M 2210/0612; A61F 9/00781; A61F 2009/00891; A61F 9/007; A61F 9/00736
See application file for complete search history.

(56) References Cited

U.S. PATENT DOCUMENTS

| | | | | |
|---|---|---|---|---|
| 3,726,284 | A * | 4/1973 | Parker | 604/8 |
| 4,380,239 | A * | 4/1983 | Crawford et al. | 604/28 |
| 4,524,771 | A * | 6/1985 | McGregor et al. | 606/223 |
| 5,021,043 | A * | 6/1991 | Becker et al. | 606/192 |
| 5,092,837 | A * | 3/1992 | Ritch et al. | 604/8 |
| 5,180,362 | A * | 1/1993 | Worst | 604/8 |
| 5,437,625 | A * | 8/1995 | Kurihashi | 604/8 |
| 5,735,829 | A * | 4/1998 | Cherian | 604/264 |
| 6,547,765 | B1 * | 4/2003 | Walsh et al. | 604/264 |
| 7,431,709 | B2 | 10/2008 | Pinchuk et al. | |
| 7,594,899 | B2 | 9/2009 | Pinchuk et al. | |
| 7,837,644 | B2 | 11/2010 | Pinchuk et al. | |
| 2002/0188308 | A1 * | 12/2002 | Tu et al. | 606/167 |
| 2005/0125034 | A1 * | 6/2005 | Cichocki | 606/222 |
| 2008/0228127 | A1 | 9/2008 | Burns et al. | |
| 2010/0114006 | A1 * | 5/2010 | Baerveldt | 604/8 |
| 2011/0118835 | A1 * | 5/2011 | Silvestrini et al. | 623/6.14 |
| 2013/0184631 | A1 | 7/2013 | Pinchuk | |
| 2014/0171750 | A1 * | 6/2014 | Fay et al. | 600/300 |
| 2014/0243729 | A1 * | 8/2014 | Rynerson | 604/8 |

OTHER PUBLICATIONS

Alan P. Ladd; Marc S. Levy; Jennifer Quilty. Minimally invasive technique in treatment of complex, subcutaneous abscesses in children. Journal of Pediatric Surgery. vol. 45, Issue 7, Jul. 2010, pp. 1562-1566.*

* cited by examiner

*Primary Examiner* — Adam Marcetich

(74) *Attorney, Agent, or Firm* — Gordon & Jacobson, PC (57) ABSTRACT

A system is provided including an elongate needle body and an aqueous humor drainage device. The drainage device includes an elongated flexible tube that is operatively coupled to a proximal end of the needle body. Methods for the implantation of the aqueous humor drainage device in the eye are provided. A system including an elongate needle body and drainage device is also provided for draining other body cavities.

28 Claims, 7 Drawing Sheets

METHODS, SYSTEMS AND DEVICES FOR TREATING GLAUCOMA

CROSS-REFERENCE TO RELATED APPLICATIONS

This application claims priority from U.S. Provisional Patent Appl. No. 61/908,657, filed on Nov. 25, 2013, herein incorporated by reference in its entirety.

BACKGROUND

1. Technical Field

The present disclosure relates to the treatment of glaucoma. More particularly, the present disclosure relates to medical devices and methods for creating a drainage pathway to divert aqueous humor out of the anterior chamber of the eye such that pressure within the eye is reduced.

2. State of the Art

Glaucoma, a progressive ocular disease that manifests itself through elevated intraocular pressure ("IOP"), is one of the leading causes of preventable blindness. When the pressure in the eye remains sufficiently high for a long enough period of time, blindness or total vision loss may occur. If properly treated, the pressure within a glaucomic eye may be reduced and the possibility of blindness may be averted.

Figure 1:
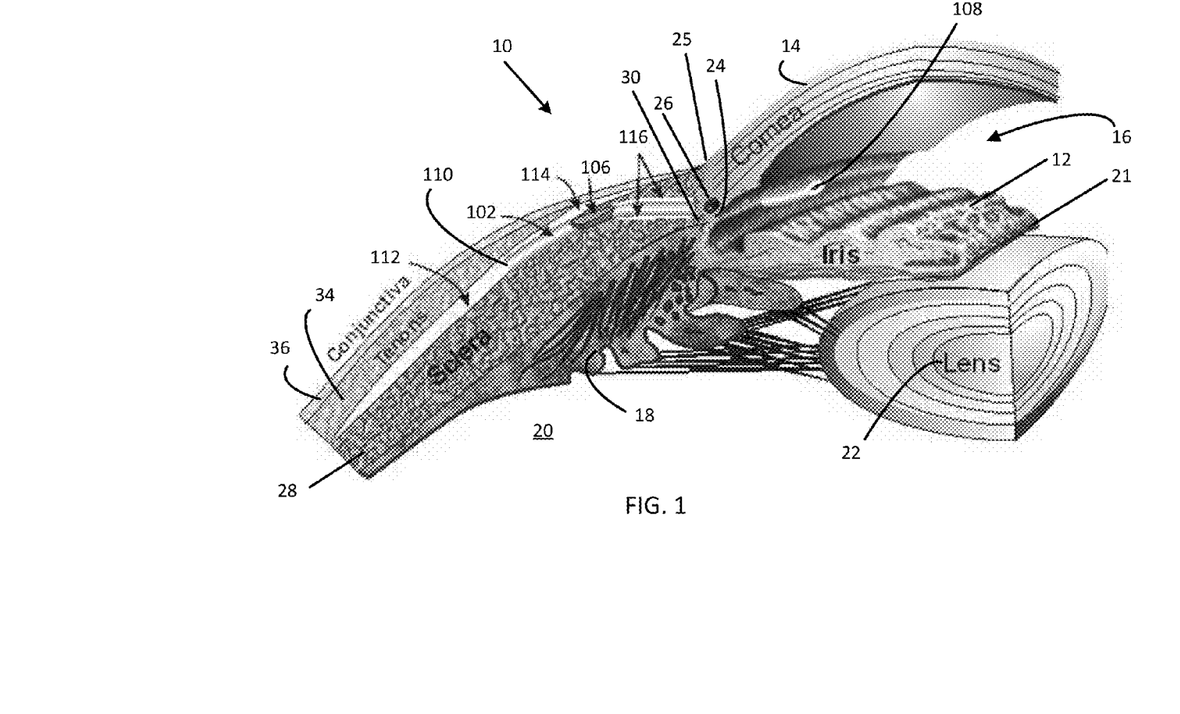
FIG. 1 is a perspective view of a prior art aqueous humor drainage device.

The anatomy of the eye is described with reference to FIG. 1. The eye 10 includes an iris 12, which is a colored circular muscle that controls the size of the pupil 21, which is an opening located in the center of the iris 12. By adjusting the size of the pupil 21, the amount of light that is allowed to enter the eye can be adjusted in response to light conditions. A cornea 14, which is a transparent external surface, covers the pupil 21 and the iris 12. The area of the eye above the lens 22 and under the cornea 14 comprises the anterior chamber 16.

The sclera 28, which is the white of the eye, is a tough outer membrane that covers the entire eye 10, except for the portion of the eye 10 that is covered by the cornea 14. The area or junction where the cornea 14 merges into the sclera 28 is known as the limbus 25. A portion of the sclera 28 is covered by a thin tissue called the Tenon's membrane (also called the Tenons Capsule) 34, which envelopes the bulb of the eye 10 from the optic nerve (not shown) to the ciliary body 18 of the eye 10. The conjunctiva 36 lines the inside of the eyelids (not shown) and overlies the Tenon's membrane 34 and the sclera 28.

The trabecular meshwork 24 is a wedge-shaped structure composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. The trabecular meshwork 24 and the Schlemm's canal 26 are located at or near the angle 30, which is the angle formed at the vertex of the iris 12 and the cornea 14. The outer wall of the trabecular meshwork 24 coincides with the inner wall of Schlemm's canal 26.

Schlemm's canal 26 is a tube-like structure that runs around the circumference of the cornea 14. In human adults, Schlemm's canal 26 is believed to be divided by septa into a series of autonomous, dead-end canals. Aqueous humor travels through the spaces between the trabecular beams of the trabecular meshwork 24, into Schlemm's canal 26, and through a series of collecting channels that drain from Schlemm's canal 26 and into the episcleral venous system (not shown).

The anterior chamber 16, which is the space between the iris 12 and the cornea 14, contains a clear fluid called aqueous humor, which is essential for the proper functioning of the eye. Aqueous humor is formed by the ciliary body 18 which is adjacent to the posterior chamber 20 of the eye 10. The aqueous humor, which is made at a fairly constant rate, passes around the lens 22, through the pupil 21 in the iris 12 and into the anterior chamber 16. The aqueous humor naturally drains out of the anterior chamber 14 primarily through the trabecular meshwork 24 and Schlemm's canal 26.

In a normal patient, aqueous humor production is equal to aqueous humor outflow and intraocular pressure remains fairly constant, typically in the 8 to 18 mmHg range. If the production of aqueous humor is not balanced by its proper drainage, the aqueous humor will build up to a high level of intraocular pressure (or IOP) and cause glaucoma.

Various devices have been designed to treat glaucoma by alleviating the IOP within the eye. Examples of such devices may be found in U.S. Pat. Nos. 7,431,709; 7,594,899; 7,837,644; and U.S. Pat. Pub. No. 2013/0184631, the contents of each of which are incorporated herein in their entireties.

Figure 2:
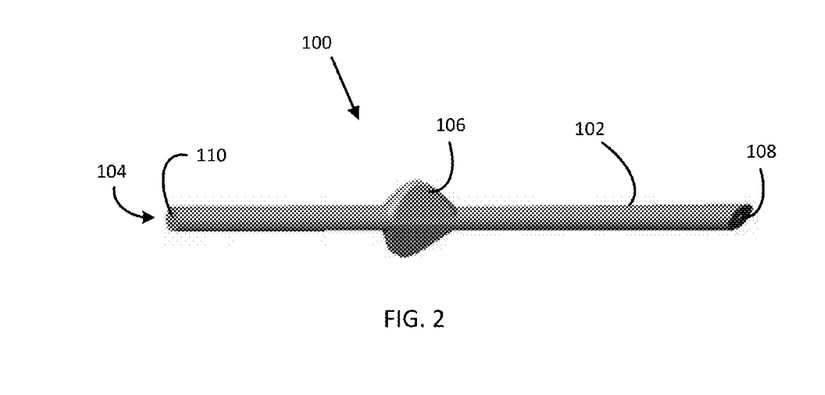
FIG. 2 is an illustration showing anatomic details of the human eye with the prior art aqueous humor drainage device of FIG. 1 implanted therein.

One such device for treating glaucoma will now be described with reference to FIGS. 1 and 2. A drainage implantation device 100 includes a tube 102 having a lumen 104 extending lengthwise through the tube 102, and a protrusion or fin 106 extending radially outward from the exterior of the tube 102 as shown in FIG. 2. The fin 106 is configured to prevent the tube 102 from migrating and to prevent the leakage of aqueous humor from around the tube 102 (i.e., peri-annular leakage) once the device 100 is implanted in a patient's eye as shown in FIG. 2. The tube 102 has an inlet end 108 disposed opposite an exit end 110. During implantation, the inlet end 108 is positioned within the anterior chamber 16 of the eye, and the exit end 110 is positioned within a space (or pouch) 114 that is formed primarily between Tenon's membrane 34 and the sclera 28 by physical dissection of the conjunctiva 36 and Tenon's membrane from the sclera 28 with scissors as evident from FIG. 2. The tube 102 extends through a needle tract 116 through the sclera 28 leading to the anterior chamber 16. The needle tract 116 may be formed from a 25 gauge (G) needle (which is approximately 0.020" or 0.51 mm in diameter). The inlet end 108 of the tuber 102 can have a diameter that is approximately 0.013" or 0.33 mm, which is smaller than the diameter of the needle, which facilitates maneuvering of the inlet end 108 through the needle tract 116 into the anterior chamber 16. The fin 106 has a diameter than is larger than the diameter of the needle and thus larger than the needle tract 116. In this configuration, the fin 106 may be wedged into scleral tissue of the needle tract 116 and act as a stopper where the scleral tissue seals against the exterior surface of the fin 106 and thus prevent peri-annular leakage. Preventing such uncontrolled leakage of aqueous humor out of the anterior chamber 16 is desirable because hypotony (very low IOP) may otherwise result, thereby damaging the eye.

The device 100 may be delivered to the implantation site via a hollow needle. To reduce the possibility of damaging the eye from the insertion of the needle therethrough, it is desirable that the needle be as narrow as possible. However, since the device 100 is to translate through the needle, the needle must necessarily have a greater diameter than that of the device 100. Often, such needles have incorporated slots, extending along the length of the needle to accommodate the fin 106 of the tube 102 of the device 100 as the tube 102 translates through a lumen extending lengthwise through the needle.

Unfortunately, the use of a slotted, hollow needle may present a few noteworthy challenges and difficulties. For example, a slotted needle may not penetrate the sclera 28 of the eye 10 as easily as a needle that does not have such a slot. In particular, the missing section of the slotted needle may impede the insertion of the needle through the sclera 28. Therefore, the force necessary to penetrate the sclera 28 may be greater when using a slotted needle as compared to a needle that does not have such a slot. Since it is desirable that the forces required to insert the needle through the sclera be as small as possible such that the possibility of trauma to the eye is kept to a minimum, the use of a slotted needle poses a challenge. Another challenge may be translating the implant, e.g., device 100, to the implantation site as it may be difficult to push a relatively soft tube through a hollow needle because the soft tube may expand sufficiently to become jammed in the hollow space of the needle.

SUMMARY

Disclosed herein are systems, devices, and methods for the treatment of ocular pressure.

In an embodiment, a system for the treatment of ocular pressure may include a needle device and an aqueous humor drainage device. The needle device may include an elongate needle body that has a sharp distal end and a proximal end. The needle may have a configuration or shape that is straight or curved, and may have a gauge (or diameter) that is between 30 G and 22 G inclusive (a smaller gauge number corresponding to a larger sized diameter). The aqueous humor drainage device may include an elongate flexible tube with two opposed ends. One end of the flexible tube may be operatively coupled to the proximal end of the needle body. The tube can have an outer diameter that is at least as large as (or greater than) the maximum diameter of the needle body or preferably, the tube can have an outer diameter that is at least as large as (or greater than) the maximum diameter of the needle passageway formed by inserting the needle through the tissue of the eye. In one embodiment, the tube can have an outer diameter that is between 100 to 600 µm.

The aqueous humor drainage device can also include one or more protrusions that extend radially outward from the exterior surface of the intermediate portion of the tube. Such protrusion(s) can be bulbous in shape or simple flares or bumps in the tube, if desired. The protrusion(s) can be either symmetrical or non-symmetrical around the axis of the tube. Such protrusion(s) can function to aid in fixing the position of the aqueous humor drainage device in the preferred location in the eye. In addition, the tube can include a visual indicator (such as a mark) that indicates a proper place where the drainage tube should be placed, cut or otherwise trimmed, if needed.

The aqueous humor drainage device may be formed from a variety of materials. In an embodiment, the tube is formed from a material that is capable of bending and assuming the curvature of the eye. In an embodiment, the aqueous humor drainage device may be formed from a material that is capable of bending and assuming a curvature of the eye when implanted therein. Furthermore, the aqueous humor drainage device may be formed from a material that is bio-stable or not bio-reactive. For example, the aqueous humor drainage device may be formed from a synthetic thermoplastic polymer such as a polyolefin, e.g., poly(styrene-block-isobutylene-block-styrene) (SIBS).

In another embodiment, a method for the treatment or prevention of glaucoma may include providing a system that includes a needle device and an aqueous humor drainage device. The needle device may include an elongate needle body that has a sharp distal end and a proximal end. The aqueous humor drainage device may include an elongate flexible tube with opposed first and second ends. The first end of the tube may be operatively coupled to the proximal end of the needle body. The outer diameter of the tube may be at least as great as the maximum diameter of the needle body. The method may further include inserting the sharp distal end of the needle body through an entrance site in eye tissue to form tissue passageways leading to and from the anterior chamber of the eye, and pushing the needle body through such tissue passageways such that the sharp distal end of the needle body exits from an exit site of tissue spaced from the entrance site and extends beyond the exit site. The exposed portion of the needle body that extends beyond the exit site can be grasped and pulled such that the needle body and tube are pulled through the tissue passageways with at least the first end of the tube that is coupled to the proximal end of the needle body extending beyond the exit site of the needle. A portion of the tube adjacent the first end that extends beyond the exit site is then decoupled from the proximal end of the needle body, for example by cutting the first end portion of the drainage tube at a desired location spaced from the proximal end of the needle body. A drainage bleb (e.g., a blister-like space) can be defined by eye tissue near either the exit site or the entrance site of the needle. For example, the drainage bleb can be defined between the conjunctiva/Tenon's membrane and the sclera over a localized portion of the eye tissue adjacent the exit site or the entrance site. In one embodiment, the drainage bleb is defined by eye tissue near the exit site, and the first end portion of the tube that extends beyond the exit site is positioned such that it is positioned inside the drainage bleb, and the opposed second end of the tube is positioned inside the anterior chamber of the eye. In another embodiment, the drainage bleb is defined by eye tissue near the entrance site, and the first end portion of the drainage tube is positioned inside the anterior chamber of the eye, and the opposed second end of the tube that extends beyond the entrance site is positioned inside the drainage bleb. In either configuration, the tube is positioned such that it provides fluid communication between the anterior chamber of the eye and the drainage bleb to allow for aqueous humor to drain from the anterior chamber of the eye through the tube into the drainage bleb.

Various approaches for implanting the aqueous humor drainage device are disclosed. In one embodiment, referred to herein as an ab interno approach, the distal end of the needle body is inserted into an entrance site at the cornea near the limbus. The needle body is advanced through the cornea and into the anterior chamber, where it is advanced through the anterior chamber under the cornea until the distal end hits the angle of the eye. The needle body is advanced further through the angle into the sclera below the limbus. The needle body is further maneuvered through the sclera below the limbus where its distal tip emerges at an exit site spaced from the entrance site. The needle body is pushed further such that the distal end of the needle body extends beyond the exit site to expose a distal portion of the needle body adjacent the distal end. The exposed distal portion of the needle body that extends beyond the exit site can be grasped and pulled (for example, with a needle clamp) such that the needle body and tube are pulled through the tissue passageways defined by the needle body with at least the first end of the tube that is coupled to the proximal end of the needle body extending beyond the exit site. The opposed second end of the tube is positioned inside the anterior chamber of the eye. The drainage bleb is defined by eye tissue near the exit site. The first end portion of the tube that extends beyond the exit site of the needle is then decoupled from the proximal end of the needle and possibly trimmed if need be. The first end portion of the tube is then positioned such that the end of the tube that extends beyond the exit site is positioned inside the drainage bleb. In this configuration, the tube is positioned such that it provides fluid communication between the anterior chamber of the eye and the drainage bleb to allow for aqueous humor to drain from the anterior chamber of the eye through the tube into the drainage bleb.

In another embodiment, referred to herein as an ab externo approach, the distal end of the needle body is inserted into an entrance site in the conjunctiva near the limbus (or in the sclera near the limbus in the event that the conjunctiva is pulled away from the sclera at the entrance site). The needle body is then pushed such that its distal end advances through the sclera under the limbus until its distal end enters the anterior chamber at or near the angle of the eye. The needle body is further advanced through the anterior chamber of the eye such that it pierces the cornea and emerges at an exit site in the cornea spaced from the entrance site. The needle body is pushed further such that the distal end of the needle body extends beyond the exit site to expose a distal portion of the needle body adjacent the distal end. The exposed distal portion of the needle body that extends beyond the exit site can be grasped and pulled (for example, with a needle clamp) such that the needle body and tube are pulled through the tissue passageways defined by the needle body with at least the first end of the tube that is coupled to the proximal end of the needle extending beyond the exit site. The first end portion of the tube that extends beyond the exit site is then decoupled from the proximal end of the needle. The drainage bleb is defined by eye tissue near the entrance site of the needle. The opposed second end of tube that extends beyond the entrance site can be grasped and pulled such that the opposed first end portion of the tube is positioned inside the anterior chamber of the eye. The second end of tube that extends beyond the entrance site can be trimmed, if necessary, and positioned inside the drainage bleb. In this configuration, the tube is positioned such that it provides fluid communication between the anterior chamber of the eye and the drainage bleb to allow for aqueous humor to drain from the anterior chamber of the eye through the tube into the drainage bleb.

In a still further embodiment, a medicant may be injected or applied to the eye to reduce the possibility of complications from the procedure. The medicant may include, for example, an antiproliferative or antimetabolite agent, e.g., mitomycin C, 5-fluorouracil, etc. The medicant may also include other agents such as lidocaine, epinephrine, steroids, etc.

The entrance site (and possibly parts of the tissue passageways leading into the anterior chamber of the eye) can be formed by the needle body or be an incision that was formed in the eye for another procedure, such as an incision for removal of a cataractous lens for traditional phacoemulsification of the natural crystalline lens of the eye.

These and other aspects of the present disclosure are more fully described hereinbelow with reference to accompanying figures in which the same reference numerals refer to like or similar elements.

DETAILED DESCRIPTION

As used herein, the term "distal" is generally defined as in the direction of the eye of the patient, or away from a user of the system, apparatus, and/or device. Conversely, "proximal" generally means in the direction away from the eye of the patient or toward the user of the system, apparatus, or device. As used herein, the word "diameter" refers to the greatest diameter or width of an object along a length thereof, and does not necessarily mean that the object being referred to has a cross-section that is a circle (e.g., the object may have a cross-section that is generally circular or oval-shaped).

Figure 3A:
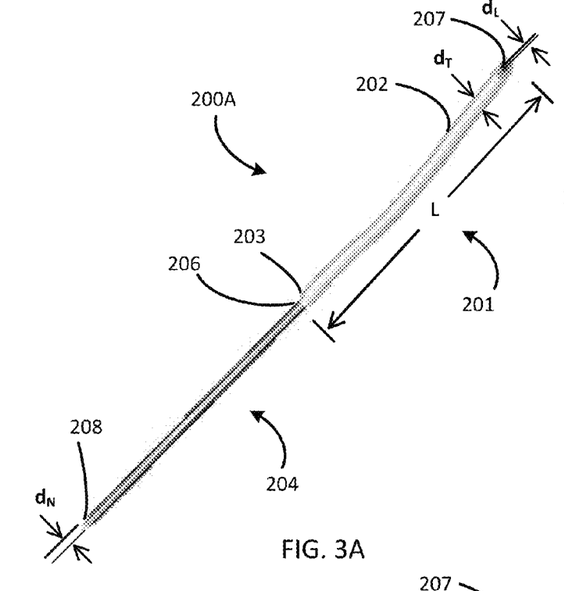
FIG. 3A is a perspective view of a first embodiment of an aqueous humor drainage system including a drainage implant tube and a straight needle.
Figure 3B:
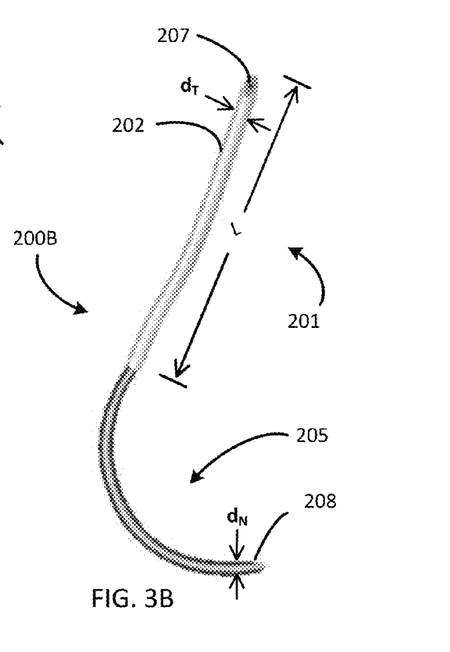
FIG. 3B is a perspective view of a second embodiment of an aqueous humor drainage system including an aqueous humor drainage implant tube and a curved needle.

Embodiments of an aqueous humor drainage system for the treatment of glaucoma are described herein with reference to FIGS. 3A and 3B. As shown in FIG. 3A, an aqueous humor drainage system 200A may include an aqueous humor drainage device 201 including an aqueous humor drainage tube (or "drainage tube) 202, and may also include a needle device defined by an elongate needle body 204 operatively coupled to the drainage tube 202. For example, one end 203 of the drainage tube 202 may be operatively coupled to a proximal end 206 of the needle body 204 by an adhesive, a swagged fitting, a crimping, a whipping, or combinations thereof. The transition of the needle body 204 to the drainage tube 202 can be abrupt or the end of the drainage tube 202 that is coupled to the proximal end 206 of the needle body 204 can possibly be tapered to provide a tapered transition that facilitates smooth pull-through. The drainage tube 202 can also be molded around the filament of a conventional suture that is coupled to the proximal end 206 of the needle body 204. The needle body 204 has a sharp distal tip 208. The needle body 204 is configured to lead the drainage tube 202 through tissue passageways through eye tissue, which may be formed by the translation of the needle body 204 through the eye tissue toward an implantation site within the eye. The drainage tube 202 may be severable or capable of being cut such that the needle body 204 may be uncoupled from the drainage tube 202, wherein the needle body 204 may be discarded once the drainage tube 202 is positioned at a desired location. The needle body 204 may have a sufficiently short length such that it may be used in areas around the cornea 14 without interfering with the forehead or nose of the patient as may occur if a long, rigid inserter were utilized for the implantation of the drainage tube 202 in the eye 10.

The drainage tube 202 may be configured to be implanted within the eye to divert aqueous humor away from the anterior chamber 16 of the eye 10. The drainage tube 202 may have generally tubular configuration. In particular, the drainage tube 202 may have a generally tubular shape having an elongate generally cylindrical shape, and may include a lumen 207 extending along its length through which fluid may pass. The drainage tube 202 may have an outer diameter $d_T$ that is between 100 and 700 μm, inclusive, and may preferably be between 200 and 500 μm, inclusive. The lumen 207 may have a diameter $d_L$ that is between 30 and 200 μm, inclusive, and may preferably be between 40 and 120 μm, inclusive. The drainage tube 202 may have an overall length L that is between 1 and 30 mm, inclusive, and may be trimmed in situ to a desired length that may be between 4 and 15 mm.

The needle body 204 may have an elongate, generally cylindrical configuration or shape, and may be generally straight as shown in FIG. 3A. The needle body 204 may also include a tapered or pointed distal end 208 that may facilitate puncturing and insertion of the needle body 204 through eye tissue without creating an opening that is larger than the gauge of the needle body 204. The interior (not shown) of the needle 204 may be solid or hollow. The needle body 204 may be formed from any conventional needle material including, but not limited to, a metal, such as stainless steel, chrome plated steel, titanium, etc.

The needle body 204 may be generally straight, as shown in FIG. 3A. However, the needle body may have any shape or configuration that facilitates the implantation of the drainage tube 202. In FIG. 3B, an aqueous humor drainage system 200B is shown that is substantially similar to the system 200A except in the ways that will now be described. In particular, the system 200B includes needle body 205 that is generally curved. It is to be understood, that needle bodies having other shapes or configurations may be incorporated into the systems 200A and 200B. For example, a needle body having a variety of shapes, for example, multiple curves, may replace the needle body 204 or 205 of the systems 200A and 200B, respectively.

Each of the needle bodies 204 and 205 of the systems 200A and 200B, respectively, may have a maximal outer diameter $d_N$ that is relatively smaller than the exterior diameter $d_T$ of the drainage tube 202. In one embodiment, the maximum exterior diameter $d_N$ of the needle body 204 or 205 may have a gauge that ranges from 30 G (approximately 0.0122" or 0.3112 mm) to 22 G (approximately 0.02825" or 0.7176 mm). The ratio of outer diameter $d_N$ of the drainage tube 204 to the outer diameter $d_N$ of the needle body may be in the range of 1 to 3, and more preferably in the range of 1.1 to 1.8.

The sharp or distal end 208 of needle body 204 of system 200A or needle body 205 of system 200B may include bevels (not shown) that are capable of cutting a hole through tissue as well as dilating tissue. Moreover, a hole that is formed in tissue as a result of the needle body being inserted through the tissue may correspond to or equal the gauge or thickness of the needle body. When the needle body is retracted from the tissue tract (or tissue passage) which it has formed, the diameter of the tissue tract may shrink. For example, if the needle body is 25 G in diameter, the hole when the needle body is in place may be 25 G. However, upon retraction of the needle body, the tissue tract, which is formed by the insertion of the needle body through the tissue, may shrink to about 27 G. The extent of the shrinkage may correspond to the sharpness and geometry of the distal end of the needle body. Accordingly, the diameter $d_T$ of the drainage tube 202 may be approximately the same size or somewhat larger than the diameter $d_N$ to effectively fill and lodge within the tissue tract to prevent or inhibit peri-annular leakage around the drainage tube 202 and migration of the drainage tube 202 from within the tissue tract formed by the needle body. Moreover, the drainage tube 202 may be formed from a compressible or semi-compressible material such that the drainage tube 202 becomes elongated in length with a reduced outer diameter as it is pulled through the tissue tract and is biased to return toward its natural length and outer diameter where there is no pulling forces applied to the drainage tube 202. In this case, when the pulling of the drainage tube 202 is ceased with the drainage tube 202 located in the tissue tract, the drainage tube 202 can relax back toward its natural original diameter and lodge in the tissue tract thereby preventing peri-annular leakage as well as preventing migration of the drainage tube 202 within the tissue tract. Moreover, the elasticity of the tissue of the tissue tract may accommodate the reception of a slightly larger sized diameter tube 202 such that the drainage tube 202 is received snuggly therein.

Figures 3C, 3D:
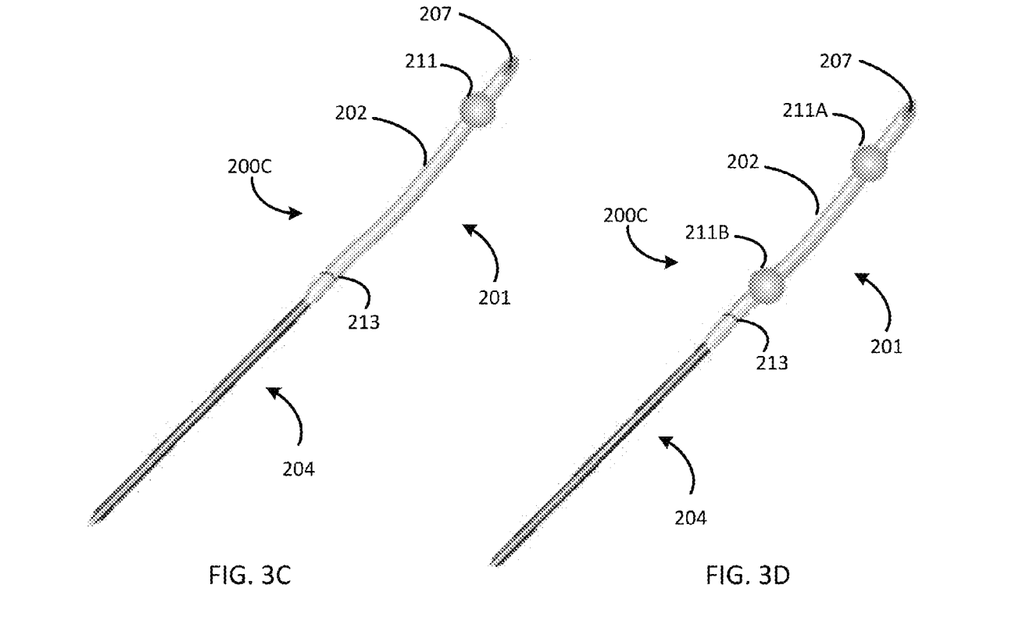
FIG. 3C is a perspective view of a third embodiment of an aqueous humor drainage system including a drainage implant tube with a protrusion and a straight needle.
FIG. 3D is a perspective view of a fourth embodiment of an aqueous humor drainage system including a drainage implant tube with a plurality of protrusions and a straight needle.

As shown in FIGS. 3C and 3D, one or more protrusions 211 can extend radially outward from the exterior of the drainage tube 202 at an intermediate position offset between the opposed ends of the drainage tube. The embodiment of FIG. 3C includes one protrusion 211. The embodiment of FIG. 3D includes two protrusions 211A and 211B that are spaced apart from one another along the length of the drainage tube 202. The protrusion(s) 211 can be bulbous in shape if desired. Such protrusion(s) can function to aid in positioning and fixing the drainage tube 202 in the preferred location in the eye. In addition, the drainage tube 202 can include a visual indicator (such as a mark 213 as shown in FIGS. 3C and 3D) that indicates a proper place where the drainage tube 202 should be cut or severed or decoupled from the needle and/or trimmed, if needed.

Figure 3E:
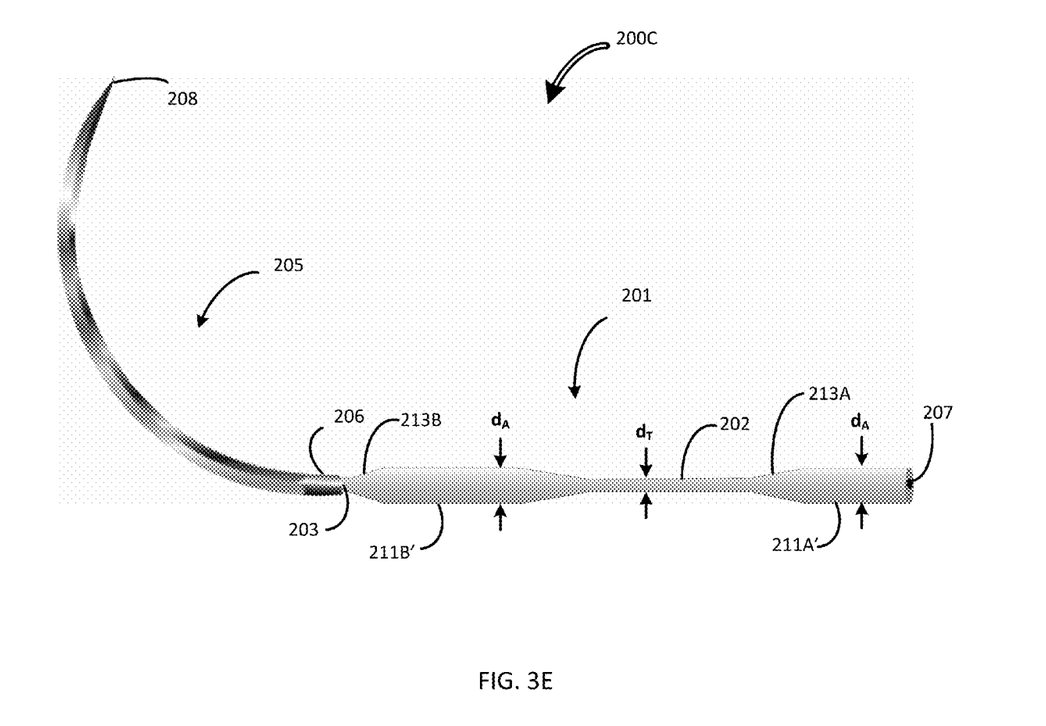
FIG. 3E is a perspective view of a fifth embodiment of an aqueous humor drainage system including an aqueous humor drainage implant tube and a curved needle.

FIG. 3E shows an aqueous humor drainage system 200C that is similar to the system 200B with a curved needle body 205. The curved needle body 205 has a triangular cross-section whose apex cutting edge is located on the outside of the needle body curvature. The proximal end 206 of the needle body 205 is hollow to define a cavity that receives the end 203 of the drainage tube 202. The outer diameter of the end 203 of the drainage tube 202 is less than inner diameter of the hollow cavity of the proximal end 206 of the needle body 205. Adhesive can be applied to the end 203 of the drainage tube 202 before it is inserted into the hollow cavity of the proximal end 206 of the needle body 205, and then the adhesive can be allowed to cure to operably couple the end 203 of the drainage tube 202 to the proximal end 206 of the needle body 205. Alternatively, the proximal end 206 of the needle body 205 can employ a swagged fitting, a crimping, a whipping, combinations thereof or other suitable fastening mechanism that operably couples the end 203 of the drainage tube 202 to the proximal end 206 of the needle body 205. The drainage tube 202 of the embodiment of FIG. 3E includes two anchor sections 211A' and 211B' that are spaced apart from one another on opposite ends of the drainage tube 202. The anchor sections 211A' and 211B' each have maximum outer diameter $d_A$ that is greater than the outer diameter $d_T$ of the intermediate tube section that extends between the two anchor sections 211A' and 211B' as shown. The end of the anchor section 211A' that is located opposite the free end of the drainage tube 202 (and thus closer to the proximal end 206 of the needle body 205) can have a surface 213A with a tapered profile that extends radially outward while tapering away from the end 203 of the drainage tube 202. The end of the anchor section 211B' that is located adjacent the end 203 of the drainage tube (and near the proximal end 206 of the needle body 205) can have a surface 213B with a tapered profile that extends radially outward while tapering away from the end 203 of the drainage tube 202. The tapered surfaces 213A and 213B of the anchor sections 211A' and 211B' can function to aid in reducing resistance while pulling the drainage tube through the needle tract defined by the needle body 205. The anchor sections 211A' and 211B' themselves can function to aid in positioning and fixing the drainage tube 202 in the preferred location in the eye in the same manner described herein with respect to the protrusion(s) of the embodiments of FIGS. 3C and 3D.

The aqueous humor drainage device (tube) as described herein may be formed from a material that is capable of bending and assuming the curvature of the eye once implanted therein. Furthermore, the material forming the aqueous humor drainage device (tube) is preferably relatively bio-inert such that, after implantation, the production of inflammation and fibrosis at or around the implantation site is minimal. In one embodiment, the aqueous humor drainage device may be formed of a bio-stable material, e.g., SIBS (poly(styrene-block-isobutylene-block-styrene). The use of such materials may reduce the possibility that the lumen 207 of the drainage tube 202 may become obstructed over time following its implantation within the eye.

In other embodiments, the aqueous humor drainage device (tube) may be formed of a synthetic thermoplastic polymer including but not limited to polyolefin, e.g., SIBS, polyethylene, polypropylene, SEBS (styrene-ethylene/butylene-styrene), etc. Other materials that may form the aqueous humor drainage device 201 may include polyurethanes, such as polyetherurethanes, polycarbonate urethanes, copolymers of polyurethane with silicone-diols, polyisobutylene-diols, polyfluoro-diols, etc. The aqueous humor drainage device 201 may also be formed of flupopolymers, for example, polytetrafluoroethylene (PTFE), fluorinated ethylene propylene (FEP), polyvinylidene fluoride or polyvinylidene diflouride (PVDF), etc. Other more rigid polymers that can be pre-shaped, such as polymide, polysulfone, etc., may be used to form the aqueous humor drainage device (tube). Still other materials that may be used to form the aqueous humor drainage device (tube) include biological polymers such as collagen, elastin, gelatin, polysaccharides, etc. The aqueous humor drainage device (tube) can be formed by extrusion molding of the synthetic thermoplastic polymer. Other suitable thermoplastic forming methodologies can also be used such as injection molding, insert molding, solvent casting, etc.

While it is desirable that the lumen 207 of the drainage tube 202 be free of tissue ingrowth that may block or obstruct the flow of fluid therethrough, an exterior or outer surface of the drainage tube 202 may be configured to facilitate tissue ingrowth such that the migration or relative motion between the tissue bed and the drainage tube 202 is prevented, thereby facilitating permanent anchoring of the drainage tube 202 at the implantation site after its implantation. It may also be advantageous in certain embodiments to have the wall of the tube fenestrated to provide multiple inflow and outflow paths to and from the lumen in the event the ends of the lumen become occluded.

Prior to the procedures for implanting the aqueous humor drainage device 201, which are described below with reference to FIGS. 4A to 7, a fluid, such as a viscoelastic fluid, may be pumped into the anterior chamber 16 of the eye 10 to create an enlarged space for the reception of the aqueous drainage system therethrough. The viscoelastic fluid may be removed from the eye by aspiration at the end of the procedure. Moreover, other fluids such as mitomycin C may be injected under the conjunctiva/Tenons to create a hydrated area that functions as a localized drainage bled. Note that this localized drainage bled is formed in a different manner that physical dissection of the conjunctiva 36 and the Tenon's membrane 34 of the eye 10 from the sclera 28 as described above with reference to FIGS. 1 and 2. The creation of the drainage bleb can involve swabbing or milking the tissue following the injection to press the raised area toward the limbus of the eye. The aqueous humor drainage device 201 may be implanted in fluid communication with the drainage bleb such that aqueous humor can be diverted from the anterior chamber 16 into the drainage bleb following the implantation of the aqueous humor drainage device 201. The injection of Mitomycin C may occur at the time of surgery or preferably 30 minutes to several days prior to surgery to allow the Mitomycin C to soak into the tissue as opposed to forming puddles of Mitomycin C. The reason puddles of Mitomycin C are avoided is to prevent it back-flowing through the drainage shunt into the anterior chamber which can cause trauma to the cornea and other organelles of the eye.

Figure 4A:
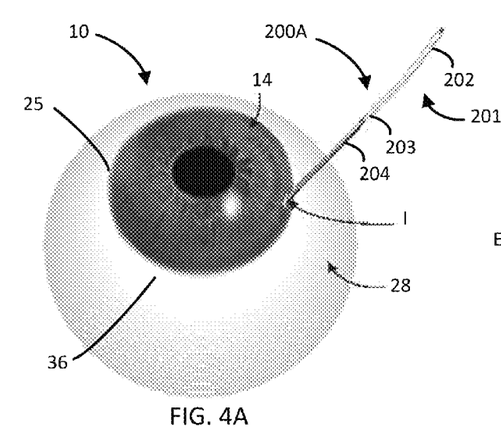
FIGS. 4A-4D are perspective views illustrating a first embodiment of a method using the aqueous humor drainage system of FIG. 3A for the implantation of an aqueous humor drainage implant tube within an eye.
Figure 4B:
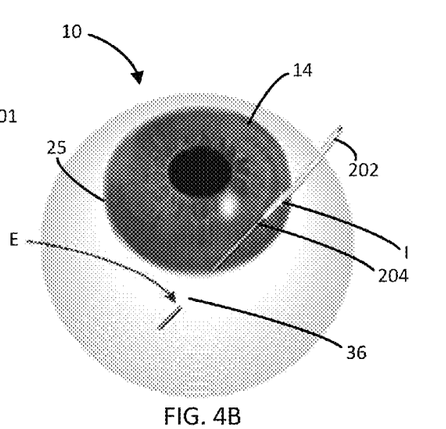
Figure 4C:
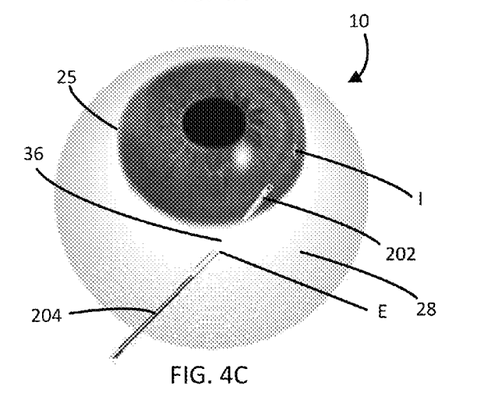
Figure 4D:
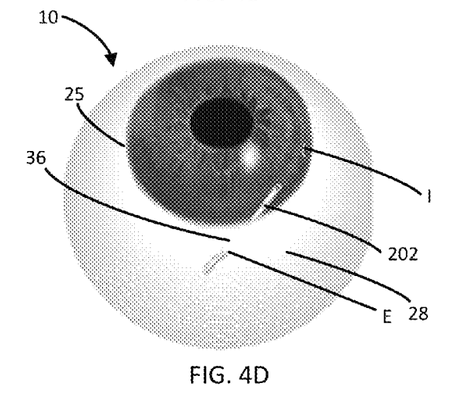

With reference to FIGS. 4A-4D, an ab interno approach will now be described that utilizes the aqueous humor drainage system 200A of FIG. 3A to implant the aqueous humor drainage device 201. As shown in FIG. 4A, the distal end 208 of the needle body 204 may penetrate the cornea 14 at entrance site I (or, if done subsequent to cataract surgery, a slit in the clear cornea may already be in place at entrance site I). The drainage bled is formed near the exit site E as described below. The needle body 204 may be pushed such it is advanced through the entrance site I in the cornea 14 into the anterior chamber 16 and then through the anterior chamber 16 until the distal tip 208 contacts the angle 30 of the eye 10. The needle body 204 is pushed to advance and maneuver the needle body 204 through the sclera 28 below the limbus 25 such that the distal tip 208 emerges through the sclera 28 (and/or any overlying conjunctiva 36) at the exit site E. At this point, the distal end of the needle body 204 extends beyond the exit site E to expose a distal portion of the needle body 204 adjacent the distal end of the needle body 204 as shown in FIG. 4B. The exposed distal portion of the needle body 204 can be grasped and pulled (for example, with a needle clamp (not shown)) such that the needle body 204 and the drainage tube 202 are pulled through the tissue passageways defined by the advancement of the needle body 204 through the tissue of the eye 10 with at least the end 203 of the drainage tube 202 that is coupled to the proximal end of the needle 204 extending beyond the exit site E as shown in FIG. 4C. The exposed distal portion of the needle body 204 may be grasped and pulled to pull the drainage tube 202 until a length of the drainage tube 202 drops below the cornea 14 and remains in the anterior chamber 16 of the eye, and a portion of the drainage tube 202 extends out from the sclera 28 beyond the exit site E. In this configuration, 1 to 3 mm of the drainage tube 202 can remain in the anterior chamber 16 of the eye. Thereafter, the portion of the drainage tube 202 that extends beyond the exit site E may be severed or cut or otherwise decoupled from the needle body 204, and the needle body 204 may be discarded while leaving the drainage tube 202 implanted within the eye 10. The severing or cutting or decoupling of the drainage tube can occur at a visual indicator (such as visual indicator 213 shown in FIGS. 3C and 3D). The remaining tail of the drainage tube 202 that extends beyond the exit site E can then be positioned inside the drainage bleb. The unshaded portion of the eye 10 in FIGS. 4A-4D illustrate the conjunctiva 36 can be pushed anteriorly, scrunched up, or retracted toward the limbus 25 (moved out of the way) to enable the needle to penetrate the conjunctiva posteriorly (towards the head). Penetration posteriorly is preferred as the conjunctiva/Tenons are thicker and will heal quicker with less chance of leakage as compared to an anterior penetration. Once the needle 204 is severed from the tube 202, the conjunctiva 36 may then be swabbed, moved back, or sutured at or near its initial position such that the exposed end of the drainage tube 202 that extends beyond the exit site E is positioned inside the drainage bleb and anteriorly from the exit wound. Thereafter, any external opening in the eye, e.g., the entrance site I formed by the needle 204, may be sealed, for example, by cauterizing, suturing or gluing such an opening. In this configuration, the drainage tube 202 is positioned such that it provides fluid communication between the anterior chamber of the eye and the drainage bleb to allow for aqueous humor to drain from the anterior chamber of the eye through the lumen 207 of the drainage tube 202 into the drainage bleb.

Figures 5A, 5C:
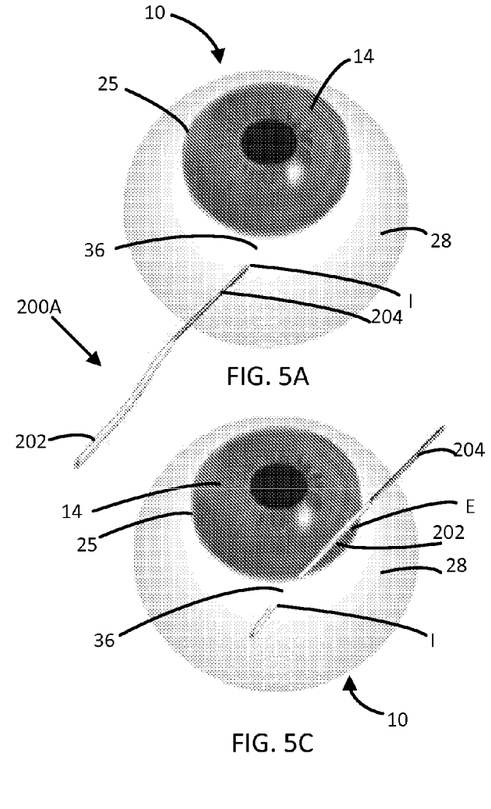
FIGS. 5A-5D are perspective views illustrating a second embodiment of a method using the aqueous humor drainage system of FIG. 3A for the implantation of an aqueous humor drainage implant tube within an eye.
Figure 5B:
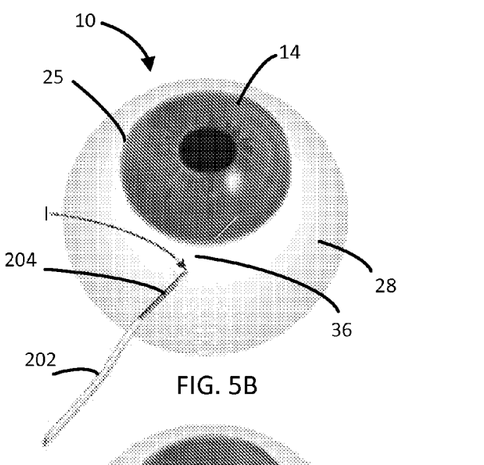
Figure 5D:
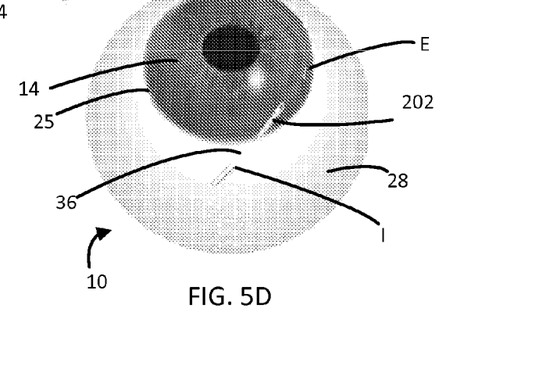

With reference to FIGS. 5A-5D, an ab externo approach will now be described that uses the aqueous humor drainage system 200A of FIG. 3A to implant the aqueous drainage device 201. In an area near the entrance site I where the needle body 204 is to be inserted, the conjunctiva 36 may be scrunched up or milked anteriorly to enable penetration of the conjunctiva/Tenons through a thicker section to allow for better healing as well as to locate the conjunctiva wound in an area remote from the end of the drainage tube. As shown in FIGS. 5A and 5B, the distal end 208 of the needle body 204 may be pushed such that it penetrates through the conjunctiva 36 (if not retracted) and the sclera 28 at the entrance site I. The needle body 204 may be advanced such that the distal tip 208 is advanced under the limbus 25 and enters into the anterior chamber 16 at or near the angle 30 of the eye and passes through the anterior chamber 16 under the cornea 14 as shown in FIG. 5B. The distal end 208 of the needle body 204 may be advanced further until the distal end 208 penetrates and extends out from the cornea 14 at an exit site E in the cornea 14 as shown in FIG. 5C. The needle body 204 is pushed further such that the distal end 208 of the needle body 204 extends beyond the exit site E to expose a distal portion of the needle body 204 adjacent the distal end 208. The exposed distal portion of the needle body 204 that extends beyond the exit site E can be grasped and pulled (for example, with a needle clamp (not shown)) such that the needle body 204 and the drainage tube 202 are pulled through the tissue passageways defined by the advancement of the needle body 204 with at least the end 203 of the drainage tube 202 that is coupled to the proximal end of the needle body 204 extending beyond the exit site E as shown in FIG. 5C. The exit end portion of the drainage tube 202 that extends beyond the exit site E is then severed or cut or decoupled from the proximal end of the needle body 204. The severing or cutting or decoupling of the drainage tube 202 can occur at a visual indicator (such as visual indicator 213 shown in FIGS. 3C and 3D). Thereafter, the needle body 204 may be discarded. The drainage bleb is defined by eye tissue near the entrance site I. The opposed free end of drainage tube 202 that extends beyond the entrance site I can be grasped and pulled such that the opposed exit end portion of the drainage tube 202 is retracted into a position inside the anterior chamber 16 under the cornea 14 as shown in FIG. 5D. In this configuration, 1 to 3 mm of the drainage tube 202 can remain in the anterior chamber 16 of the eye. The free end of drainage tube 202 that extends beyond the entrance site I can be trimmed, if necessary, and positioned inside the drainage bleb. If the conjunctiva 36 was pushed anteriorly, scrunched up, or retracted toward the limbus 25, the portion of the conjunctiva me may be returned to its initial position, for example, by using sutures or may be forced back into its initial position or simply relax back to its initial position. Thereafter, any external opening in the eye, e.g., the exit site E formed by the needle body 204, may be sealed if necessary, for example, by cauterizing, gluing or suturing such an opening. In this configuration, the drainage tube 202 is positioned such that it provides fluid communication between the anterior chamber of the eye and the drainage bleb to allow for aqueous humor to drain from the anterior chamber of the eye through the lumen 207 of the drainage tube 202 into the drainage bleb.

Figure 6A:
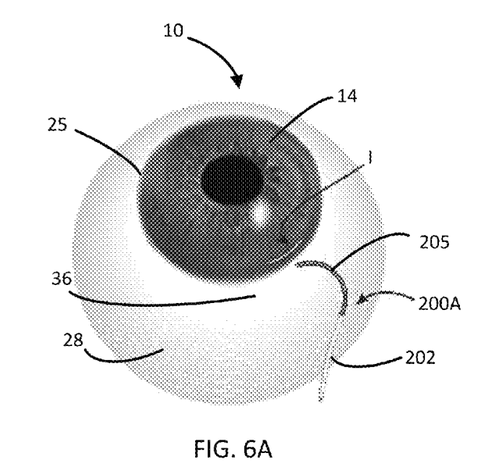
FIGS. 6A-6D are perspective views illustrating a third embodiment of a method using the aqueous humor drainage system of FIG. 3B for the implantation of an aqueous humor drainage implant tube within an eye.
Figure 6B:
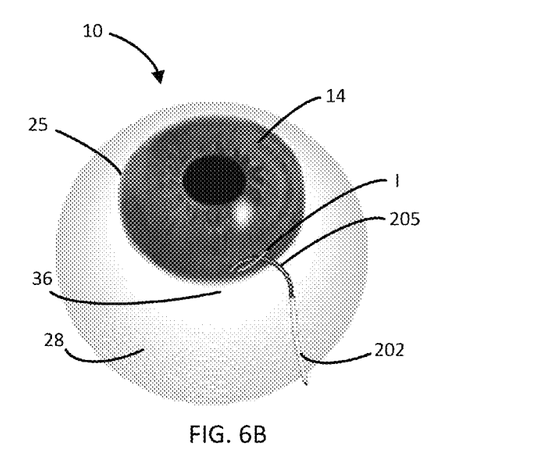
Figure 6C:
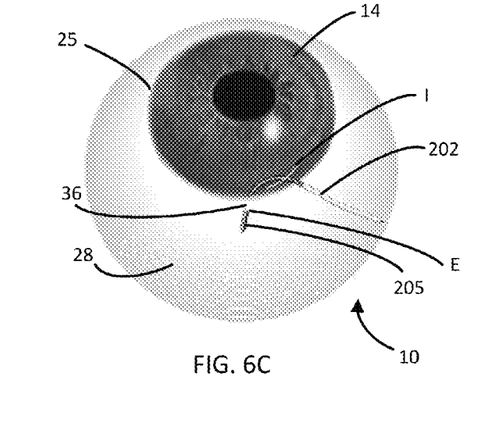
Figure 6D:
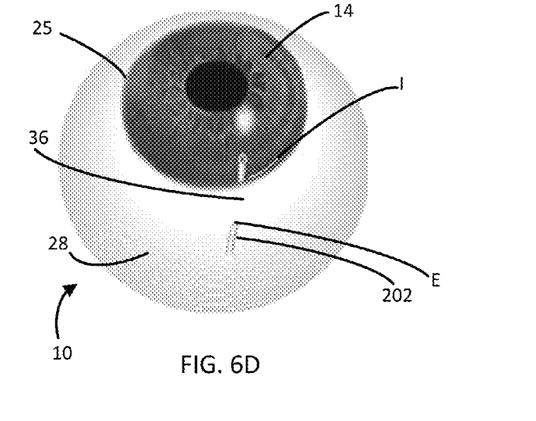

With reference to FIGS. 6A-6D, an ab interno approach will now be described that utilizes the aqueous humor drainage system 200B of FIG. 3B to implant the aqueous drainage device 201. As shown in FIG. 6A, the distal end 208 of the curved needle body 205 may penetrate the cornea 14 at entrance site I. Note that the entrance site I may be the clear corneal incision formed during a cataract surgery procedure. The drainage bleb is formed near the exit site E as described below. The needle body 205 may be maneuvered such it is advanced through the entrance site I in the cornea 14 into the anterior chamber 16 as shown in FIG. 6B and then through the anterior chamber 16 until the distal tip 208 contacts the angle 30 of the eye 10. The needle body 205 is maneuvered further such that the distal end 208 extends through the sclera 28 below the limbus 25 and then pierces the sclera 28 (and/or any overlying conjunctiva 36 or Tenons 34) at the exit site E. At this point, the distal end of the needle body 205 extends beyond the exit site E to expose a distal portion of the needle body 205 adjacent the distal end of the needle body 205 as shown in FIG. 6C. The exposed distal portion of the needle body 205 can be grasped and pulled (for example, with a needle clamp (not shown)) such that the needle body 205 and the drainage tube 202 are pulled through the tissue passageways defined by the advancement of the needle body 205 through the tissue of the eye 10 with at least the end of the drainage tube 202 that is coupled to the proximal end of the needle body 205 extending beyond the exit site E. The exposed distal portion of the needle body 205 may be pulled to pull the drainage tube 202 until approximately 1 to 3 mm of the drainage tube 202 remains in the anterior chamber 16, and a portion of the drainage tube 202 extends out from the sclera 28 beyond the exit site E. Thereafter, a portion of the drainage tube 202 that extends beyond the exit site E may be severed or cut or decoupled from the needle body 205, and the needle body 205 may be discarded while leaving the drainage tube 202 implanted within the eye 10. The severing or cutting or decoupling of the drainage tube 202 can occur at a visual indicator (such as visual indicator 213 shown in FIGS. 3C and 3D). The exposed end of the drainage tube 202 that extends beyond the exit site E is then positioned inside the drainage bleb formed near the exit site E. In doing so, the exposed end of the drainage tube may be placed or tucked under the conjunctiva 36 and/or Tenon's membrane 34, and any conjunctiva 36 that was retracted or bunched up may be restored to its initial position. Thereafter, any external opening in the eye, e.g., the entrance site I formed by the needle body 205, may be sealed if necessary, for example, by cauterizing, suturing or gluing such an opening. In this configuration, the drainage tube 202 is positioned such that it provides fluid communication between the anterior chamber of the eye and the drainage bleb to allow for aqueous humor to drain from the anterior chamber of the eye through the lumen 207 of the drainage tube 202 into the drainage bleb.

An ab interno approach can be used in conjunction with the aqueous humor drainage system of FIG. 3E to implant the aqueous humor drainage device into the eye in a manner similar to the ab interno approach that is discussed above with reference to FIGS. 6A-6D. Furthermore, an ab externo approach can be used in conjunction with the aqueous humor drainage system of FIGS. 3B and 3E to implant the aqueous humor drainage device into the eye in a manner similar to the ab externo approach that is discussed above with reference to FIGS. 5A-5D.

Figure 7:
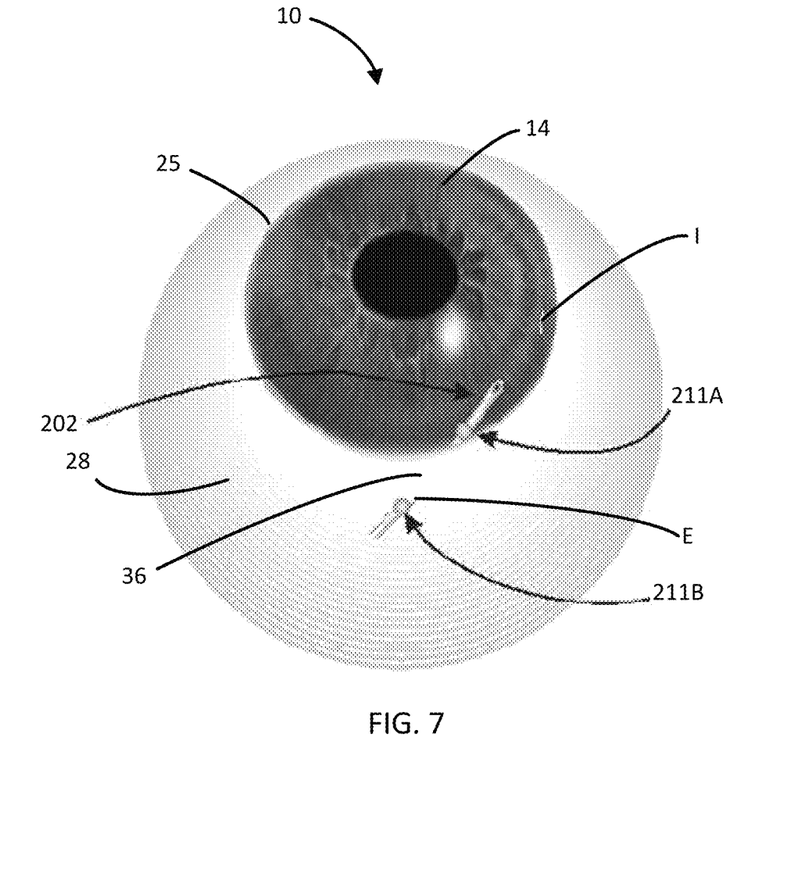
FIG. 7 is a perspective view illustrating the aqueous humor drainage implant tube of FIG. 3D within an eye.

FIG. 7 shows the aqueous humor drainage tube 202 of FIG. 3D having two protrusions 211A and 211B, which is implanted into the eye using the ab interno approach of FIGS. 4A-4D (or 6A-6D). The protrusions 211A and 211B can aid in positioning and fixating the drainage tube 202 in its desired position as shown in FIG. 7. Specifically, the protrusion 211A is positioned inside the anterior chamber 16 of the eye and can add resistance to the pull force applied to the exit site end of the drainage tube 202 as the drainage tube 202 is pulled through the tissue tract created by the needle body 204 and the protrusion 211A contacts the tissue near the angle and the limbus of the eye. Furthermore, the length offset between the protrusion 211A and the free end of the drainage tube 202 can be used to ensure the desired length of drainage tube remains in the anterior chamber 16 of the eye. The protrusion 211B is positioned near the exit site E and can aid in fixation by minimizing movement of the drainage tube 202 toward the anterior chamber 16 of the eye.

For the ab externo approach of FIGS. 5A-5D, the protrusions 211A and 211B can also aid in positioning and fixating the drainage tube 202 in its desired position. In this case, the protrusion 211B is positioned inside the anterior chamber 16 of the eye and can add resistance to the pull force applied to the entrance site end of the drainage tube 202 as the drainage tube 202 is refracted and the protrusion 211B contacts the tissue near the angle and the limbus of the eye. Furthermore, the length offset between the protrusion 211B and the severed end of the drainage tube 202 can be used to ensure the desired length of drainage tube remains in the anterior chamber 16 of the eye. The protrusion 211A is positioned near the entrance site I and can aid in fixation by minimizing movement of the drainage tube 202 toward the anterior chamber 16 of the eye which can occur when the patient blinks. Although FIG. 7 shows two protrusions, there need only be one protrusion located either on the distal or proximal end of the tube 202.

Note that the entrance site (and possibly parts of the tissue passageways leading into the anterior chamber of the eye) can be formed by the needle body or be an incision that was formed in the eye for another procedure (such as an incision required to remove the cataractous lens of the patient and to perform the traditional phacoemulsification procedure). Furthermore, the tract through the sclera can be formed with a conventional needle or knife prior to insertion of the drainage tube.

In a still further embodiment, the procedure can be performed using a medicant as an adjuvant to the procedure. The medicant may include, for example, an antiproliferative or antimetabolite agent, e.g., mitomycin C, 5-fluorouracil, etc. The drug can be injected under the conjunctiva 36 and Tenon's membrane 34 prior to performing the procedure. The drug can be sponged into place, eluted from the implant, added after the implant is in place and/or added in combination with all of the above. In addition, the drug can be injected in place in combination with lidocaine, epinephrine or other drugs such as antibiotics and the like.

There have been described and illustrated herein several embodiments of devices, systems, and methods for the treatment of glaucoma. While particular embodiments of the invention have been described, it is not intended that the invention be limited thereto, as it is intended that the invention be as broad in scope as the art will allow and that the specification be read likewise. Thus, while particular systems, devices and methods have been disclosed, it will be appreciated that other devices and methods may fall within the scope and spirit of the present disclosure. Specifically, these embodiments need not be restricted to glaucoma nor to the field of ophthalmology. A similar drainage system can be used to treat hydrocephalies by shunting from spaces containing cerebral spinal fluid to body cavities at a lesser pressure. Similarly, bursas and the like can be drained with this system. It will therefore be appreciated by those skilled in the art that yet other modifications could be made to the provided invention without deviating from its spirit and scope as claimed.

What is claimed is:

1. A method for the treatment of ocular pressure comprising:
   providing a system including a needle device and an aqueous humor drainage device, wherein the needle device includes a needle body having a sharp distal end and a proximal end, and the aqueous humor drainage device includes an elongate flexible tube with opposed first and second ends, wherein the first end of the tube is attached to the proximal end of the needle body opposite the second end of the tube and the tube extends away from the proximal end of the needle body outside the needle body;
   inserting the sharp distal end of the needle body through an entrance site in eye tissue to form tissue passageways leading to and from the anterior chamber of the eye, and maneuvering the needle body through eye tissue such that the sharp distal end of the needle exits from an exit site in eye tissue spaced from the entrance site and extends beyond such exit site; and
   severing the tube from the proximal end of the needle body such that tube is not attached to the needle body.

2. A method according to claim 1, wherein:
   the maneuvering of the needle body involves pushing the needle body through eye tissue.

3. A method according to claim 1, wherein:
   the severing involves severing a part of the tube that extends beyond the exit site.

4. A method according to claim 1, further comprising:
   pulling a portion of the needle body that extends beyond the exit site such that the needle body and tube are pulled through the tissue passageways with at least the first end of the tube that is coupled to the proximal end of the needle extending beyond the exit site.

5. A method according to claim 1, further comprising:
   defining a drainage bleb over a localized portion of the eye tissue; and
   positioning the tube such that it provides fluid communication between the anterior chamber of the eye and the drainage bleb to allow for aqueous humor to drain from the anterior chamber of the eye through the tube into the drainage bleb.

6. A method according to claim 5, wherein:
   the drainage bleb is formed between Tenon's membrane and/or the conjunctiva and the sclera.

7. A method according to claim 5, wherein:
   the drainage bleb is defined over a localized portion of the eye tissue adjacent a portion of the tube that extends beyond the exit site; and the positioning of the tube includes positioning the portion of the tube that extends beyond the exit site into the drainage bleb and positioning the second end of the tube in the anterior chamber of the eye.

8. A method according to claim 7, wherein:
the entrance site is in the cornea of the eye, and the exit site is in the sclera or conjunctiva of the eye.

9. A method according to claim 8, wherein:
the tissue passageways formed by the needle body include a first section that extends through the cornea and into the anterior chamber of the eye and a second section that extends from anterior chamber of the eye through the sclera under the limbus of the eye.

10. A method according to claim 5, wherein:
the drainage bleb is defined over a localized portion of the eye tissue adjacent a portion of the tube that extends beyond the entrance site; and
the positioning of the tube includes pulling on the portion of tube that extends beyond the entrance site in order to position the first end portion of the tube in the anterior chamber of the eye and positioning the portion of the tube that extends beyond the entrance site into the drainage bleb.

11. A method according to claim 10, wherein:
the entrance site is in the sclera or conjunctiva of the eye, and the exit site is in the cornea of the eye.

12. A method according to claim 10, wherein:
the tissue passageways formed by the needle body include a first section that extends through the sclera under the limbus and into the anterior chamber of the eye and a second section that extends from the anterior camber of the eye and though the cornea of the eye.

13. A method according to claim 1, wherein:
the entrance site and exit site are in eye tissue on opposite sides of the limbus of the eye.

14. A method according to claim 13, wherein:
one of the entrance site and exit site is in the cornea of the eye, and the other of the entrance site and exit site is in the sclera or conjunctiva of the eye.

15. A method according to claim 1, wherein:
the needle body has at least one of the following characteristics:
a straight configuration or curved configuration, and
a gauge that is between 30 G and 22 G.

16. A method according to claim 1, wherein:
the tube has at least one of the following characteristics:
at least one section of the tube has an outer diameter that is at least as large as (or greater than) the maximum diameter of the needle body,
the ratio of the outer diameter of the tube to the outer diameter of the needle body is in the range of 1 to 3, and more preferably in the range of 1.1 to 1.8, and
an outer diameter that is between 100 µm and 700 µm.

17. A method according to claim 1, wherein:
the aqueous humor drainage device includes at least one element that extends radially outward from the exterior surface of an intermediate portion of the tube.

18. A method according to claim 17, wherein:
the at least one element is bulbous in shape.

19. A method according to claim 17, wherein:
the at least one element aids in locating and/or fixing the position of the aqueous humor drainage device in the preferred location in the eye.

20. A method according to claim 17, wherein:
the at least one element includes an element that remains in the anterior chamber of the eye after implantation of the aqueous humor drainage device into the eye.

21. A method according to claim 1, wherein:
the aqueous humor drainage device further includes a visual indicator that indicates a proper place where the tube should be cut or otherwise trimmed.

22. A method according to claim 1, wherein:
the aqueous humor drainage device is be formed from a synthetic polymer.

23. A method according to claim 1, wherein:
the entrance site is formed by the needle body or is an incision.

24. A method according to claim 1, wherein:
the tube is attached to the proximal end of the needle body by at least one of an adhesive, a swagged fitting, a crimping, a whipping, a suture or combinations thereof.

25. A method according to claim 1, wherein:
the tube is attached to the proximal end of the needle body by an abrupt transition or tapered transition.

26. A method for the treatment of ocular pressure comprising:
providing a system including a needle device and an aqueous humor drainage device, wherein the needle device includes a needle body having a sharp distal end and a proximal end, and the aqueous humor drainage device includes an elongate flexible tube with opposed first and second ends, wherein the first end of the tube is attached to the proximal end of the needle body and the tube extends away from the proximal end of the needle body outside the needle body;
inserting the sharp distal end of the needle body through an entrance site in eye tissue to form tissue passageways leading to and from the anterior chamber of the eye, and maneuvering the needle body through eye tissue such that the sharp distal end of the needle exits from an exit site in eye tissue spaced from the entrance site and extends beyond such exit site;
pulling a portion of the needle body that extends beyond the exit site such that the needle body and tube are pulled through the tissue passageways with at least the first end of the tube that is coupled to the proximal end of the needle extending beyond the exit site;
defining a drainage bleb over a localized portion of the eye tissue adjacent a portion of the tube that extends beyond the exit site; and
severing the tube from the proximal end of the needle body such that the tube is not attached to the needle body and positioning the tube such that it provides fluid communication between the anterior chamber of the eye and the drainage bleb to allow for aqueous humor to drain from the anterior chamber of the eye through the tube into the drainage bleb.

27. A method according to claim 26, wherein:
the drainage bleb is formed between Tenon's membrane and/or conjunctiva and the sclera.

28. A method according to claim 26, wherein:
the positioning of the tube includes positioning the portion of the tube that extends beyond the exit site into the drainage bleb and positioning the second end of the tube in the anterior chamber of the eye.

* * * * *